United States Patent [19]
Ahr

[11] Patent Number: 5,837,087
[45] Date of Patent: Nov. 17, 1998

[54] PROCESS FOR MAKING AND INCORPORATING ACQUISITION/ DISTRIBUTION INSERTS INTO ABSORBENT CORES

[75] Inventor: Nicholas Albert Ahr, Cincinnati, Ohio

[73] Assignee: The Procter & Gamble Company, Cincinnati, Ohio

[21] Appl. No.: 693,679

[22] Filed: Aug. 13, 1996

Related U.S. Application Data

[62] Division of Ser. No. 341,503, Nov. 17, 1994, Pat. No. 5,591,297.

[51] Int. Cl.$^6$ .................................................. B32B 31/00
[52] U.S. Cl. ........................ 156/250; 156/221; 156/293; 156/567; 604/358
[58] Field of Search ................................. 156/521, 517, 156/264, 293, 98, 108, 221, 222, 514, 556, 250, 567; 604/358, 385.1, 378, 379, 368, 369

[56] References Cited

U.S. PATENT DOCUMENTS

| | | |
|---|---|---|
| 810,129 | 1/1906 | Green . |
| 1,950,765 | 3/1934 | Winter ........................................ 223/15 |
| 2,254,217 | 9/1941 | Grupe ....................................... 93/36.6 |
| 2,551,663 | 5/1951 | Fox ........................................... 128/290 |
| 2,581,561 | 1/1952 | Shaw ........................................... 18/56 |
| 2,703,043 | 3/1955 | Novick et al. .............................. 93/61 |
| 2,929,179 | 3/1960 | George ......................................... 53/21 |
| 3,224,917 | 12/1965 | Langan .................................... 156/108 |
| 3,279,111 | 10/1966 | Morton ..................................... 40/158 |
| 3,343,543 | 9/1967 | Glassman ............................... 128/290 |
| 3,356,092 | 12/1967 | Joa ........................................... 128/287 |
| 3,408,908 | 11/1968 | Berkowitz ................................... 93/61 |
| 3,523,535 | 8/1970 | Croon ..................................... 128/285 |
| 3,654,006 | 4/1972 | Heller, Jr. et al. ....................... 156/108 |
| 3,716,430 | 2/1973 | Croon et al. ............................. 156/62.4 |
| 3,736,931 | 6/1973 | Glassman ............................ 128/290 R |

(List continued on next page.)

FOREIGN PATENT DOCUMENTS

| | | |
|---|---|---|
| 500789 | 2/1951 | Belgium . |
| 0 391 814 | 10/1990 | European Pat. Off. . |
| 3413925 A1 | 10/1985 | Germany . |
| 410702 | 5/1934 | United Kingdom . |
| WO 90/12130 | 10/1990 | WIPO . |
| WO 91/16870 | 11/1991 | WIPO . |
| WO 93/01779 | 2/1993 | WIPO . |
| WO 93/01780 | 2/1993 | WIPO . |
| WO 93/01781 | 2/1993 | WIPO . |
| WO 93/01782 | 2/1993 | WIPO . |
| WO 93/01783 | 2/1993 | WIPO . |
| WO 93/01785 | 2/1993 | WIPO . |
| WO 93/01786 | 2/1993 | WIPO . |
| WO 93/02235 | 2/1993 | WIPO . |
| WO 93/02251 | 2/1993 | WIPO . |
| WO 93/21968 | 11/1993 | WIPO . |
| WO 94/05500 | 3/1994 | WIPO . |

*Primary Examiner*—James Engel
*Attorney, Agent, or Firm*—Marshall, O'Toole, Gerstein, Murray & Borun

[57] ABSTRACT

An apparatus and process for assembling a first member and a second member is provided. The first member comprises a fluid distribution part and the second member comprises an absorbent core member having a window portion therein. The assembling apparatus comprises a conveyer mechanism for forming a transport path, a first deposition mechanism for placing a series of one of the first and second members in spaced apart relation on the conveyer mechanism, and a drum mechanism rotatably mounted adjacent the conveyer mechanism for carrying the other of the first and second members and for depositing the same onto one of the first or second members already placed on the conveyer mechanism. The apparatus further includes a second deposition mechanism for placing a series of the other of the first and second members on the drum mechanism in spaced apart relation and a drive mechanism for the conveyer and the drum mechanism for moving in timed relation the first and second members together on the conveyer mechanism and for positioning a portion of the first member in the window portion of the second member.

3 Claims, 5 Drawing Sheets

U.S. PATENT DOCUMENTS

| | | | |
|---|---|---|---|
| 3,844,288 | 10/1974 | Kiela | 128/287 |
| 3,887,414 | 6/1975 | Cohn | 156/108 |
| 4,340,058 | 7/1982 | Pierce et al. | 128/287 |
| 4,361,151 | 11/1982 | Fitzgerald | 128/285 |
| 4,490,147 | 12/1984 | Pierce et al. | 604/378 |
| 4,592,708 | 6/1986 | Feist et al. | 425/80.1 |
| 4,605,459 | 8/1986 | Voltmer et al. | 156/215 |
| 4,617,082 | 10/1986 | Oshefsky et al. | 156/447 |
| 4,762,520 | 8/1988 | Wallstrom | 604/366 |
| 5,002,814 | 3/1991 | Knack et al. | 428/85 |
| 5,134,007 | 7/1992 | Reising et al. | 428/78 |
| 5,200,248 | 4/1993 | Thompson et al. | 428/131 |
| 5,203,757 | 4/1993 | Kampen | 493/44 |
| 5,268,229 | 12/1993 | Phillips et al. | 428/400 |
| 5,334,176 | 8/1994 | Buenger et al. | 604/367 |

PROCESS FOR MAKING AND INCORPORATING ACQUISITION/ DISTRIBUTION INSERTS INTO ABSORBENT CORES

This is a divisional of U.S. application Ser. No. 08/341,503, filed Nov. 17, 1994 now U.S. Pat. No. 5,591,297.

FIELD OF THE INVENTION

This invention pertains to an apparatus and process for forming absorbent cores, such as for catamenial sanitary napkins and/or disposable diapers. More particularly, this invention pertains to an apparatus and process for forming and incorporating acquisition/distribution inserts into an absorbent core.

BACKGROUND OF THE INVENTION

A wide variety of types of structures for disposable absorbent articles used to collect body fluids are known in the art. Commercial absorbent articles include, for example, diapers, adult incontinence products, catamenials and bandages. Disposable products of this type comprise components for receiving, absorbing and retaining fluids. Typically, such articles include a liquid permeable topsheet, an absorbent core and a liquid impermeable backsheet.

Improving the performance of absorbent articles such as sanitary napkins continues to be a formidable undertaking, although a number of improvements have been made in both their materials and structures. A number of efforts have been directed to providing sanitary napkins with the ability to remain in contact with the wearer's body and to acquire body exudates immediately upon leaving the body and then to distribute the exudates throughout the absorbent core of the napkin.

Examples of such sanitary napkins are disclosed in PCT International Publication Nos. WO 93/01779 and WO 93/02251 which disclose sanitary napkins employing fibers having intra-fiber capillary channels (which may be referred to as the "Capillary Channel Fiber" patent application); and in WO 93/01780 to WO 93/01783 which disclose the use of capillary channel fibers that may be arranged in the form of a tufted bundle (or "bun") on a curved, body-shaped absorbent article (and, as a result may be referred to as the "Curved Bun" patent applications); and in WO 93/01785 and WO 93/01786 which disclose extensible and stretchable sanitary napkins; the disclosure of all of which are incorporated by reference herein.

While the sanitary napkins described in the above patent publications work quite well, the search for improved, as well as alternative, sanitary napkins (particularly to those described in the "Capillary Channel Fiber" and "Curved Bun" patent applications), however, has continued.

In addition, a need exists for a sanitary napkin that is at least as easy to construct, or preferably even easier to construct, as those sanitary napkins described in the above "Capillary Channel Fiber" and "Curved Bun" patent publications.

The present invention provides a method and apparatus to easily and efficiently fabricate disposable absorbent articles having the ability to acquire bodily exudates immediately upon leaving the body and then to distribute the exudates throughout the absorbent core of the article.

SUMMARY OF THE INVENTION

In accordance with a principle aspect of the invention, an apparatus is disclosed for assembling a first member, referred to as an acquisition/distribution member or tube, and a second member, referred to as an absorbent core member, having a window for receiving the first member, for use in absorbent products. The assembling apparatus comprises a conveyer means for forming a transport path, a first deposition means for placing a series of one of the first and second members in spaced apart relation on the conveyer means, and a drum means rotatably mounted adjacent the conveyer means for carrying the other of the first and second members and for depositing the same onto one of the first or second members already placed on the conveyer means. The apparatus further includes a second deposition means for placing a series of the other of the first and second members onto the drum means in spaced apart relation and a drive means for the conveyer means and the drum means for moving in timed relation the first and second members together on the conveyer means and for positioning a portion of the first member in the window portion of the second member.

BRIEF DESCRIPTION OF THE DRAWINGS

The invention will be better understood from the following detailed description taken in conjunction with the accompanying drawings, wherein.

DETAILED DESCRIPTION OF THE INVENTION

Figures 1, 3:
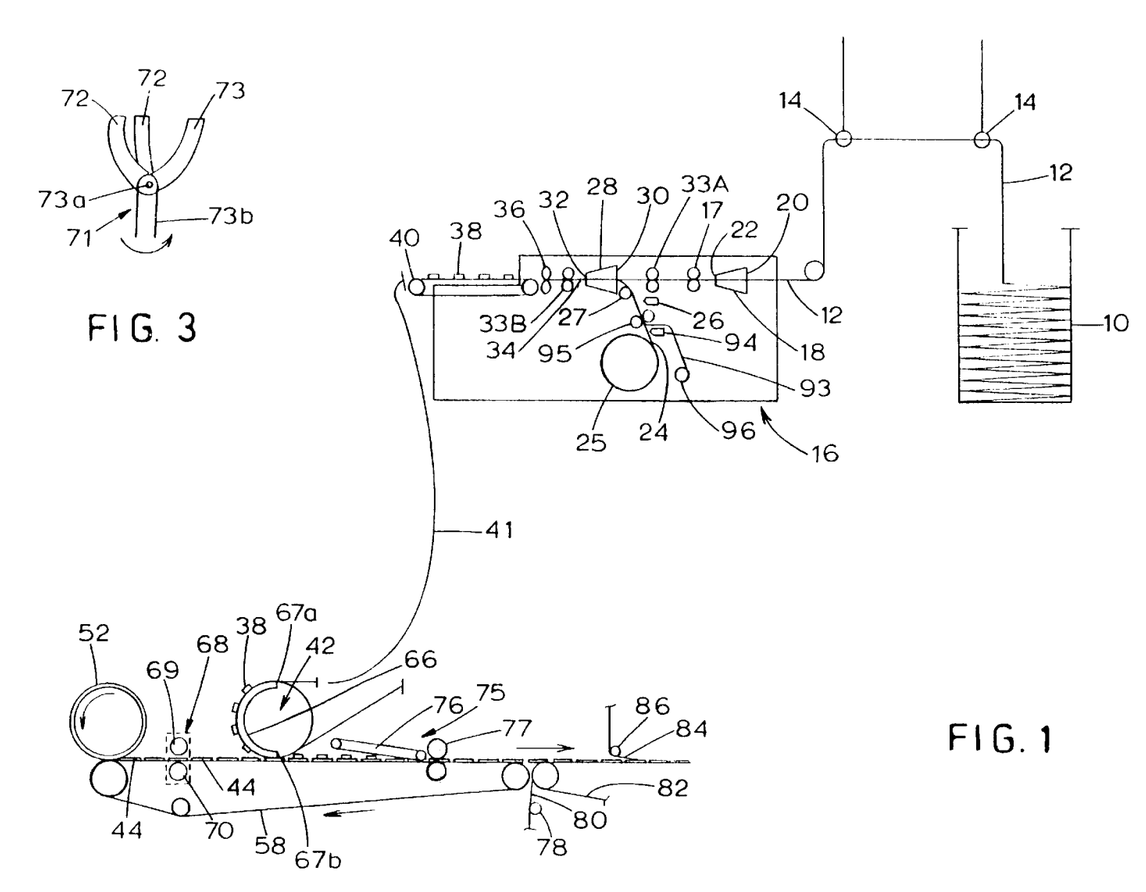
FIG. 1 is a schematic view of an apparatus constructed in accordance with a first embodiment of the present invention.
FIG. 3 is an enlarged schematic illustration of a retention/deposition member of the pickup and laydown drum of FIG. 2.

Shown schematically in FIG. 1, is an apparatus for making and incorporating an acquisition/distribution insert or tube into an absorbent core member. The apparatus includes a supply container 10 for a long tow or sliver 12. This container 10 can typically be a barrel with a spool or roll having the tow 12 wound on it. The tow 12 comprises a bundle of loose fibers, typically a bundle of 1000 or more fibers.

The fibers forming the tow 12 are preferably comprised of a material that is more resilient than comminuted wood pulp which is generally referred to as airfelt (often used as an absorbent core material). Suitable materials include, but are not limited to: capillary channel fibers, chemically modified, cross-linked cellulosic fibers, superabsorbent fibers, polyesters, rayons, orlons, foams, and surfactant treated polyolefin fibrous materials.

Preferably, the tow includes capillary channel fibers. Capillary channel fibers are fibers which have intra-fiber capillary channels, especially on their outer surface.

Suitable capillary channel fibers are described in EPO Patent Application 0 391 814 published Oct. 10, 1990; U.S. Continuation-In-Part Application entitled "Fibers Capable of Spontaneously transporting Fluids", Ser. No. 07/736,267, published as PCT WO 93/02235 on Feb. 4, 1993, filed in the name of Phillips, et al. on Jul. 23, 1991, U.S. Pat. No. 5,200,248 entitled "Open Capillary Channel Structures, Improved Process for Making Capillary Channel Structures, and Extrusion Die for Use Therein" issued in the name of Thompson, et al. on Apr. 6, 1993; and, U.S. Pat. application Ser. No. 07/918,174 entitled "Spinerette Orifices and Filament Cross-Sections With Stabilizing Legs Therefrom", filed in the name of Phillips, et al. on Jul. 23, 1992.

Suitable capillary channel fibers are also described in the following patent applications which were filed on Jul. 23, 1991: U.S. Pat. application Ser. No. 07/734,404 filed in the name of Thompson, et al.; U.S. Pat. application Ser. No. 07/734,392 filed in the name of Thompson, et al.; and, U.S. Pat. application Ser. No. 07/734,405 filed in the name of Buenger, et al. These patent applications may be referred to collectively as the "Capillary Channel Fiber" patent applications. The disclosure of all of the above patent applications and patent publications are incorporated herein by reference.

To make the tow 12 easier to handle and to transport, the tow 12 is moved through a machine 16, which may be similar to conventional machines for forming filters for cigarettes, for wrapping the fibers of the tow 12 into a tube. Referring again to FIG. 1, the tow 12 of loose fibers is drawn from the container 10 through a set of guide eyelets 14 and fed into the tube forming machine 16 by a pair of feed rollers 17. In the machine 16, the loose fibers of the tow 12 are formed into a cylindrical shape by a compressing element 18 which is funnel or horn-shaped and has first and second openings 20 and 22. The first opening 20, which is at the upstream end, has a larger diameter than the second opening 22. The size of the smaller second opening 22 determines the diameter of the tow 12 exiting the compressing element 18.

After the tow 12 has been compressed it is wrapped with a wrapping material 24 such as a non toxic tissue or other wrapping material, preferably a non-woven wrapping material, such as Unicorn Spunbond, non woven, low basis weight polypropylene manufactured by Fiberweb North America of Washaugal, Wash. As shown in FIG. 1, a supply roll 25 of sheet-like wrapping material 24 is provided in the tube forming machine 16. An adhesive is applied by a glue applicator 26 to one longitudinal edge of the wrapping material 24. A particularly useful adhesive is a construction hot melt adhesive made by Findley Adhesive, Inc. of Milwaukee, Wis., product identification number 672-334-07. The wrapping material 24 is passed over a guide roller 27 and then moved closely adjacent the tow 12 and into a tube or cylinder former 28. The cylinder former 28 is a conventional device for wrapping the tissue around the tow 12, and is preferably shaped like a G-shaped horn having a larger diameter upstream end 30 and a smaller diameter downstream end 32. The wrapping material 24 and the tow 12 are fed to the cylinder former 28 which forms or rolls the wrapping material 24 into a wrapped cylinder 34 around the tow. The edge with adhesive is overlapped with and adhered to the other longitudinal edge by the adhesive to maintain the wrapped cylinder 34 in cylindrical form so that the tow can be more easily handled.

The forming machine 16 also includes a second and a third pair of feed rollers 33A, 33B for pulling the tow 12 through the machine. As the tow 12 of fibers is wrapped in the cylinder former 28, it is maintained under tension or compression by adjusting the speed of the first, second and third pair of feed rollers 17, 33A and 33B. Preferably the second and third pair of feed rollers 33A, 33B rotate at about the same speed which is about two to about ten percent faster than the first pair of feed rollers 17. This causes the fibers of the tow 12 to be stretched and tensioned between the first and second pair of feed rollers 17, 33A. The fibers of the tow 12 are maintained and controlled under tension during the wrapping process by having the third pair of feed rollers 33B pull the wrapped cylinder 34 at about the same speed as the second pair of feed rollers 33A pulls the tow 12. The wrapping material 24 of the wrapped cylinder 34 then maintains the fibers of the tow 12 under tension until, as discussed in a greater detail below, the tension is released for in use purposes.

After the wrapped cylinder 34 leaves the cylinder former 28, it is fed to and cut into shorter length sections by a conventional cutting element 36 to form individual cylindrical acquisition/distribution tubes 38. While a variety of cutting devices may be used, the cutting element 36 preferably includes a two blade cutter in the shape of a propeller device which rotates about an axis parallel to the length or direction of movement of the tow 12. The speed of the element 36 is determined by the desired length of the acquisition/distribution tubes 38 and the rate of movement of the wrapped cylinder 34. The cutting element 36 can also be a three or four blade propeller device if additional cutting speed is required. The cutting element typically cuts the acquisition/distribution tubes 38 to lengths between three and four inches, but of course other lengths may be provided depending on the requirements of the end product.

After the acquisition/distribution tubes 38 are cut, they are deposited onto a vacuum conveyer belt 40 travelling at a higher speed than the wrapped cylinder 34 moving to the cutting element 36. As discussed further below, this increased rate of speed allows for achieving desired spacing between acquisition/distribution tubes 38 as they travel on the vacuum conveyer belt 40.

The vacuum belt 40 transports the acquisition/distribution tubes 38 to a rotatable pick-up and lay-down drum 42. A connection 41 in FIG. 1 is a schematic illustration of a conveyor connecting the conveyor 40 and the drum 42. The connection 41 may include a single vacuum conveyor belt as shown or a series of vacuum conveyor belts. The pick-up and lay-down drum 42 individually picks the acquisition/distribution tubes 38 off the connection 41, rotates and carries the acquisition/distribution tubes 38 about its periphery in an angularly spaced relation and individually deposits each tube 38 onto the top surface of an absorbent core member 44 (see FIGS. 8 and 9) previously formed.

The absorbent core member 44 can be made in any conventional way. The absorbent core member 44 is capable of absorbing or retaining liquids such as vaginal fluids (e.g., menses) and other body exudates. The absorbent core member 44 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles.

Suitable materials for the absorbent core member 44 include but are not limited to: comminuted wood pulp, which is generally referred to as airfelt; crepe cellulose wadding; tissue including tissue wraps and tissue laminates; synthetic fibers, especially polymeric fibers, such as crimped polyester fibers; meltblown polymers including coform; chemically stiffened, modified or cross-linked cellulosic fibers; fibers having intra-fiber capillary channels preferably on their exterior surfaces (capillary channel fibers); peat moss; absorbent foams; absorbent sponges; superabsorbent hydrogel-forming polymeric gelling agents; or any equivalent materials or combination of materials, or mixtures of these materials.

Figure 5:
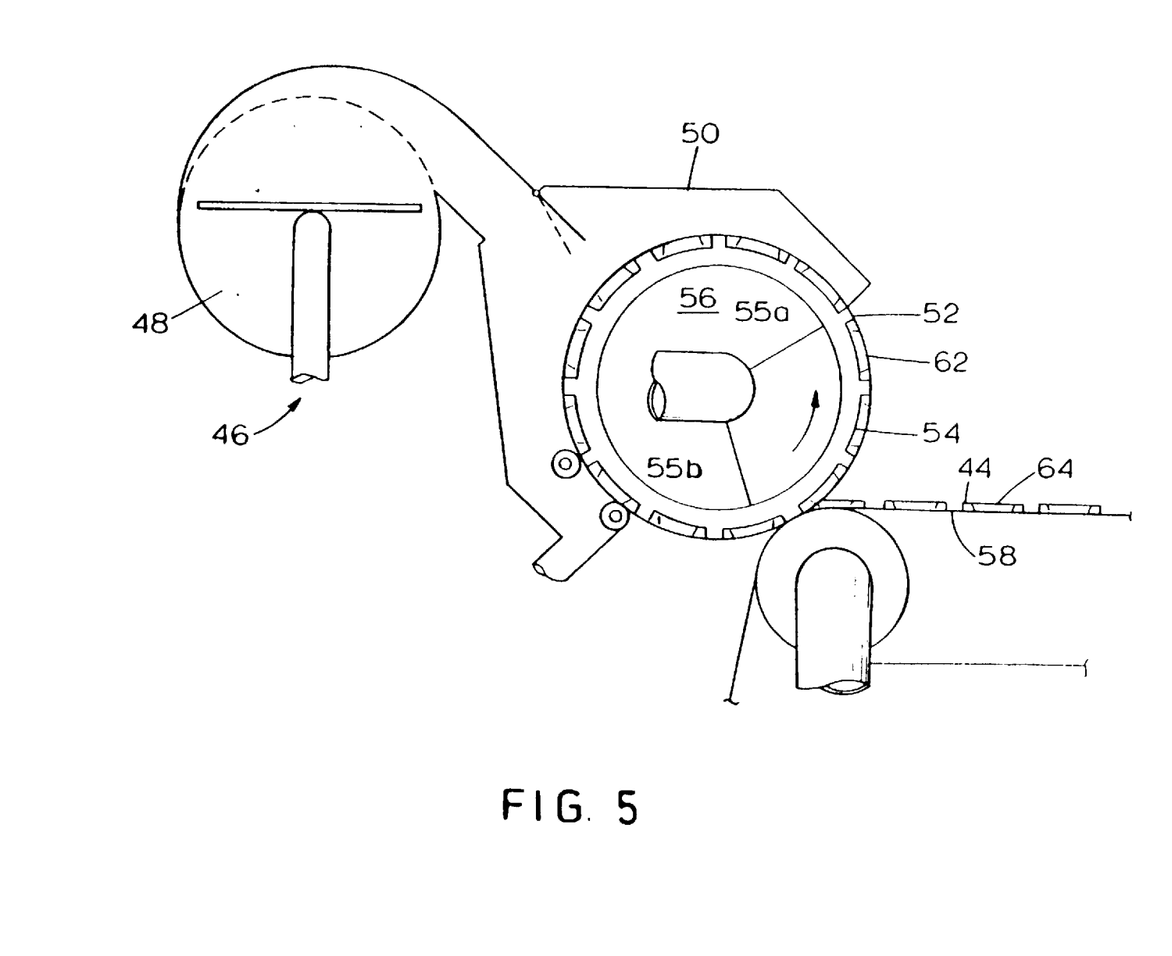
FIG. 5 is a schematic fragmentary side elevational view of an absorbent core member forming apparatus.

If the absorbent core member 44 is comprised of airfelt or other similar material, the apparatus described in U.S. Pat. No. 4,592,708 to Feist et al., the disclosure of which is incorporated herein by reference, can be used to form the absorbent core member 44. As shown in FIG. 5, an absorbent core member former machine 46 is provided. The former machine 46 includes, for example, a disc-type hammermill 48, a hood 50, a deposition drum 52 having a plurality of deposition cavities 54 disposed in circumferentially equi-spaced relation about its outer periphery, and an internal vacuum drum 56. The cavities 54 are formed of a porous or screen-like material, and the vacuum drum 56 holds the fibers in the cavities 54 from the line 55a to the line 55b.

Briefly, the hammermill 48 disassociates a drylap web (a web of wet laid, then dried cellulose fibers, not shown) and discharges a stream of entrained fibers to a short circumferential span of the periphery of the drum 52 where they are injected into the deposition cavities 54 and maintained in the cavities 54 by the vacuum drum 56 which exerts a vacuum force on the inner sides of the cavities 54. The deposition drum rotates and deposits the formed mass of fibers in each cavity 54 onto a vacuum conveyer belt 58 as an absorbent core member 44. The operation of the absorbent core former 46 is discussed in much greater detail in U.S. Pat. No. 4,592,708, referred to above.

Figure 6:
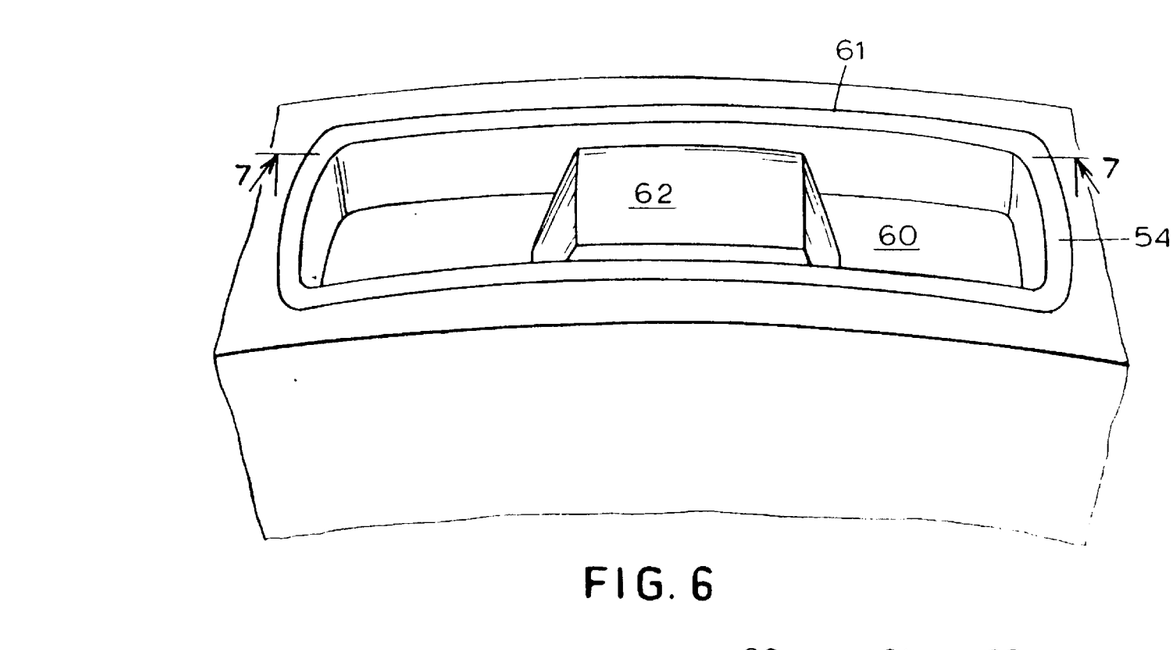
FIG. 6 is an enlarged, fragmentary side elevational view of a deposition cavity disposed on the periphery of the deposition drum of apparatus shown in FIG. 5.
Figure 7:
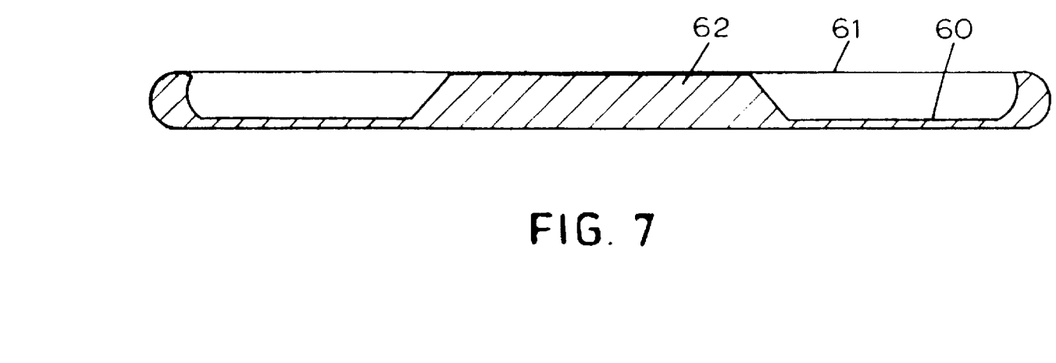
FIG. 7 is a cross sectional view taken generally along line 7—7 of FIG. 6.

The absorbent core members 44 are provided with an open area, or a window, generally free of fibers. In the specific example described herein, as shown in FIGS. 6 and 7, the deposition cavities 54 on the periphery of the drum 52 include a floor 60, an upper end 61 and a window forming portion 62. The window forming portion 62 is generally rectangular and projects up from a central portion of the floor 60 to a height substantially equal to the upper end 61 and occupies a given volume of the deposition cavity 54. The window forming portion 62 prevents fibers from the hammermill 48 from being deposited in the central portion of the cavities 54. This ensures that the central portion of absorbent core member 44 is essentially free of fibers and has an open area or a window 64 (see FIGS. 8 and 9) in its central portion. The window forming portion 62 may have a variety of dimensions preferably has a length of between 1½ to 2 inches and a width of between ½ to ¾ inch which produces a window 64 of essentially similar dimensions. The window forming portion may, of course, have other dimensions depending on the application. Also, though the window forming portion 62 is rectangular, it could have alternate configurations. For example, it could be rectangular with rounded corners, oval, elliptical or cigar shaped to produce similarly shaped windows.

Referring back to FIG. 1, if the core members 44 are not formed with a window, the machine may be provided with means (shown in dashed lines) to punch out or otherwise cut a window. In this instance, the absorbent core members 44 without a window are deposited by the deposition drum 52 onto the conveyer belt 58. To provide the absorbent core members 44 with a window, the deposited absorbent core members 44 are transported on the conveyer belt 58 to a cutout knife mechanism or section 68. This section 68 comprises a cutting roller 69 having conventional cutting means for cutting the window 64 in the absorbent core member 44 and an anvil roller 70 for supporting the absorbent core member 44 while the window is being cut. Conveyer belt 58 is preferably constructed of stainless steel or other strong material that is resistant to the cutting force of the cutting roller 69. Additionally, though not shown, instead of one conveyer belt 58, two conveyer belts which do not pass between the cutting roller 69 and the anvil roller 70, one feeding the absorbent core member 44 to the cutoff section 68 and one removing the absorbent core member 44 (now having a window 64) from cutoff section 68, can be used. This allows belts to be constructed of less cut resistant material. If the absorbent core member 44 is deposited on the conveyer belt with a window 64, the cutoff section 68 is not present.

The absorbent core members 44 having windows 64 are then transported on conveyer belt 58 to the pick-up and lay-down drum 42 which deposits an acquisition/lay-down distribution tube 38 onto the surface of each absorbent core member 44 so that a portion of the acquisition/distribution tube 38 overlies the entire length of the window 64.

The pick-up and lay-down drum 42, as shown in FIG. 1, may be a vacuum drum wherein a vacuum is applied by an arcuate internal vacuum member 66 along a span of the drum starting near the point 67a where the drum 42 picks up the acquisition/distribution tubes 38 from the connection 41 and ending near the point 67b where the acquisition/distribution tubes 38 are deposited onto the top surface of the absorbent core member 44. This span is generally illustrated by the arcuate member 66.

Figure 2:
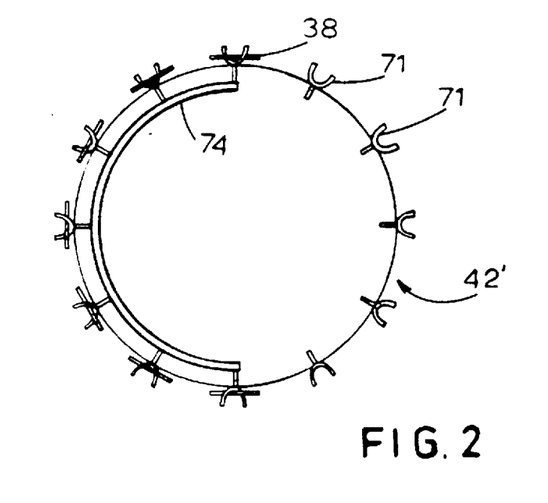
FIG. 2 is a schematic view of a mechanical tube pick-up and lay-down deposition drum in accordance with a second embodiment of the invention.

FIGS. 2 and 3, show an alternatively constructed pick-up and lay-down drum 42'. The pick-up and lay-down drum 42' includes a plurality of mechanical finger like clamps 71 disposed in a circumferentially equi-spaced relation about its outer periphery.

As best shown in FIG. 3, each of the clamps 71 has two fixed or stationary fingers 72 and a single moveable opposable thumb 73. The thumb 73 is pivotably mounted on the frame of the drum 42' by a pin 73a and it includes a radially inwardly extending part 73b. The pick-up and lay-down drum 42' also includes a stationary arcuate cam mechanism 74 which is engageable with the part 73b as the drum rotates, and thereby causes the moveable thumb 73 to pivot toward the two stationary fingers 72 to pick-up and hold an acquisition/distribution tube 38 in the clamp 71 as the clamp 71 rotates on the periphery of the rotating drum 42'. The cam mechanism 74 also causes the moveable thumb 73 to move away from the two stationary fingers 72 to release and deposit the acquisition/distribution tube 38 onto the surface of the absorbent core member 44.

The clamps 71 are preferably rotatable at least about ninety degrees about a radial line of the pick-up and lay-down drum 42'. This permits the clamp 71 to properly align the acquisition/distribution tube 38 over the window 64 of the absorbent core member 44. The cam mechanism 74 may include a portion (not illustrated) for turning the clamps 71 through a desired angle, if such turning is deemed necessary. For the best longitudinal distribution of body exudate throughout the absorbent core member 44, the acquisition/distribution tube 38 is deposited so that its long dimension (its length) aligns with the long dimension (the length) of the absorbent core member 44 so that a center portion of the tube 38 overlies the window 64. If the length of the absorbent core member 44 and the length of the acquisition/distribution tube 38 will not coincide at time of deposition, the clamp 71 can be rotated to provide for proper alignment at deposition.

After an acquisition/distribution tube 38 has been properly deposited onto the surface of an absorbent core member 44, the absorbent core member 44 with the acquisition/distribution tube 38 on its upper surface is transported on belt 58 to a compression or calendering mechanism 75 which includes a feed alignment belt 76 and a pair of compression rolls 77 (see FIG. 1). As the absorbent core member 44 and acquisition/distribution tube 38 pass through the mechanism 75, the feed alignment belt 76 first aids in maintaining the acquisition/distribution tube 38 in alignment with absorbent core member 44 and begins to compress the acquisition/distribution tube 38 into the absorbent core member 44 and then the compression rolls 77 further compress and calender the two parts together to force a portion of the acquisition/distribution tube 38 deeper into the window 64 of the absorbent core member 44.

The belt 58 preferably includes a vacuum device (not shown) for providing enough suction force to hold the tube 38 in place over the window 64 of absorbent core member 44 as they travel together on the belt 58. If desired, pockets for the members 44 may be provided on the belt.

The tubes 38 are timed to be deposited over the window of the absorbent core member 44 by what may be referred to as a cut and space process. As discussed above, the conveyer belt 40 is running at a speed faster than the speed the wrapped cylinder 34 is being fed to the cutting element 36 to enable the cut acquisition/distribution tubes 38 to be spaced from one another. The rate of rotation of the drum and the spacing of the clamps 71 must be synchronized with the tubes 38 moving on the belt 40 and with the core members 44 moving on the belt 58, so that the tubes are picked up and transferred by the drum to the core members 44. Preferably the speed of conveyer belt 40 spaces the tubes 38 at a distance substantially equal to the distance between the equi-spaced cavities 54 of the deposition drum 52 plus the difference between the length of the acquisition/distribution tube 38 and the length of the cavity 54. This allows the deposition drum 52, the pick-up and lay-down drum 42, the belt 40, the connection 41 and the belt 58 to be run at the same linear speed by a single drive timing mechanism such that the pick-up and lay-down drum 42 can properly deposit an acquisition/distribution tube 38 over the window 64 of the absorbent core member 44.

If the mechanical pick-up and lay-down drum 42' is utilized, the clamps 71 are preferably circumferentially spaced apart one from another by the same distance as the centers of the adjacent acquisition/distribution tubes 38 are spaced on the belt 40 so that the pick-up lay-down drum 42' can travel (like drum 42) at the same linear speed as belt 40, connection 41, belt 58 and deposition drum 52 and be controlled by a single drive timing mechanism. If the clamps 71 are not able to be spaced about the periphery of the drum 42' at this distance, the single drive timing mechanism may include a gearing mechanism to enable the pick-up and lay-down drum 42' to travel at a different speed than the above-enumerated apparatus elements to pick-up the acquisition/distribution tube 38 off connection 41 and properly deposit the same on an absorbent core member 44.

FIG. 1 illustrates an apparatus which manufactures absorbent products, containing the absorbent core member 44 and the acquisition/distribution tube 38, with the moisture acquisition side facing down. An absorbent product of the type described typically comprises a topsheet, a backsheet and an absorbent core sandwiched between the backsheet and topsheet. The topsheet is the acquisition side and is closest to the wearer's body and is located on what is referred to as the body facing surface of the absorbent product. The backsheet is furthest from the body or located on what is referred to as the garment facing surface of the product. As seen in FIG. 1, a topsheet unwind 78 is provided which carries a roll of liquid porous topsheet material 80. The topsheet material 80 is fed to a conveyer belt 82 so that the compressed absorbent core member 44 and acquisition/distribution tube 38 are deposited from conveyer belt 58 onto the topsheet material 80 and joined thereto by conventional means (not shown).

Conveyer belts 58 and 82 are spaced closely together so that the compressed absorbent core member 44 and acquisition/distribution tube 38 can pass from belt 58 to the belt 82 and not fall in the gap between the two belts. If necessary, a dead plate pan (not shown) may be placed between the two belts 58 and 82 to provide proper transfer between the belts and to prevent the core member 44 and the acquisition/distribution tube 38 from falling into the gap. After the compressed acquisition/distribution tube 38 and absorbent core member 44 have been deposited onto the topsheet material 80, a sheet 84 of liquid impervious backsheet material is fed from a supply roll, around an idler roll 86 and joined by conventional means (not shown) to the top of the absorbent core member 44, acquisition/distribution tube 38 and topsheet material 80. Downstream from the roll 86 are conventional devices (not illustrated) for sealing the topsheet and backsheet material together around the periphery of the core member 44 and then cutting the completed assembly into individual absorbent products such as those shown in FIGS. 8 and 9. Suitable topsheet and backsheet materials are described in co-pending U.S. Pat. application Ser. No. 08/084,048, filed in the name of Doak, et al. on Jun. 28, 1993 and entitled "Absorbent Article Having a Window With a Body-Conforming Element Positioned Therein".

Figure 8:
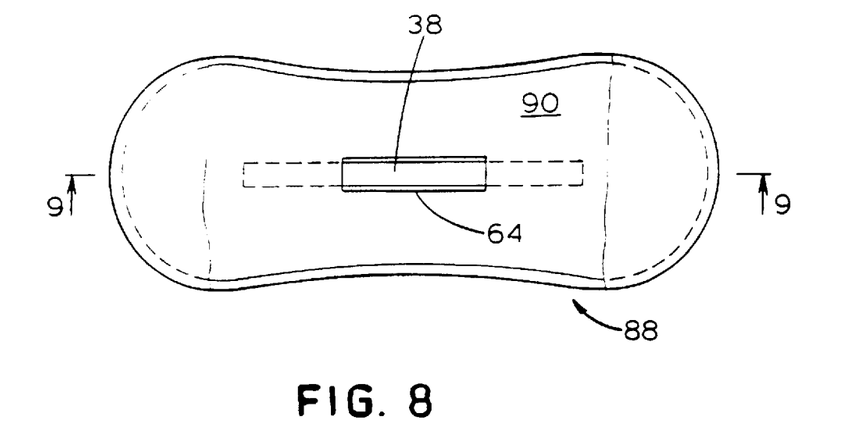
FIG. 8 is a top view of a catamenial product having an absorbent core made by the apparatus and process of the present invention.
Figure 9:
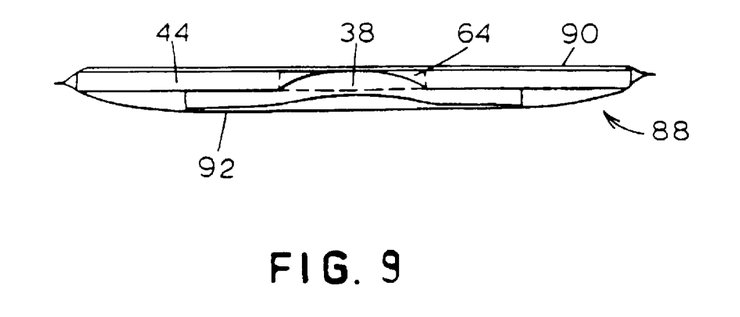
FIG. 9 is a cross-sectional view taken generally along line 9—9 of FIG. 8.

As seen in FIGS. 8 and 9, a sanitary napkin 88 has a topsheet 90 made from the topsheet material 80, and a backsheet 92 made from the backsheet material 84. Disposed between the topsheet 90 and backsheet 92 is an acquisition/distribution tube 38 and an absorbent core member 44 having a window 64. A center portion of the acquisition/distribution tube 38 is pressed into the window 64 and the end portions of the tube are between the garment facing backsheet 92 and the absorbent core member 44.

For improved body exudate fluid handling, a portion of the wrapping material 24 of the acquisition/distribution tube 38 is predisposed to open in the window 64 and release a portion of the fibers of the tow 12 into the window 64. Prior to opening, the portion of the fibers maintained in the acquisition/distribution tube 38 are stretched and held, as discussed above, under compression. The fibers are thus maintained at a given density. When the acquisition/distribution tube 38 is opened, the compression is released and the fibers of the tow 12 spread out into the window 64. The density of the released fibers is lower than the density of the fibers previously maintained in the unopened acquisition/distribution tube 38. Since the window 64 is typically designed to be located at or near the point of body exudate deposition, the lower density fibers provide an excellent acquisition zone and conform well to the wearer's body. Fluid handling characteristics of absorbent cores having similar acquisition/distribution members is discussed in much greater detail in the previously referred to co-pending U.S. Pat. application Ser. No. 08/084,048, filed in the name of Doak, et al. on Jun. 28, 1993 and entitled "Absorbent Article Having a Window With a Body-Conforming Element Positioned Therein".

It is preferred in use that only a portion of the tube 38 is opened and that only a portion of the fibers contained in the acquisition/distribution tube 38 are released into the window 64. The fibers that remain in the acquisition/distribution tube 38 have a higher density than the fibers that are released. If the fibers of the tow 12 are comprised of capillary channel fibers, the intrafiber capillary channels of the capillary channel fibers along with this density gradient helps wick the body exudate deposited in the window 64 containing the lower density released fiber to the higher density fibers remaining in the unopened portion of the acquisition/distribution tube 38 and consequently to the longitudinal ends of the absorbent core member 44.

The wrapping material 24 of the acquisition/distribution tube 38 can be pre-disposed to open for or during use of the product in a variety of ways. For example, as shown in FIG. 1, a moisture sensitive string 93 has portions permanently attached to the wrapping material 24 so that the string runs along the length of the wrapping material 24 and extends along the length of the acquisition/distribution tube 38. The string may be attached by most any means including a non-water soluble adhesive which may be the same hot-melt adhesive as the adhesive applied by the glue gun applicator 26 to the wrapping material 24. As shown in FIG. 1, a glue applicator 94 sprays glue spots on the wrapping material 24 immediately upstream of a pair of compression feed rolls 95. These rolls 95 draw both the wrapping material 24 from the roll 25 and the string 93 from its roll 96 and compress and adhere portions of the string 93 to the sprayed glue spots on the wrapping material 24 leaving a portion of the string 93 unattached. The moisture sensitive string 93 may be most any string which contracts upon exposure to moisture such as body exudate or to exposure to humidity from a wearer's body. This contraction either aids in or causes the wrapping material 24 to rupture allowing the release of fibers of the tow into the window.

Alternatively, or in addition, the wrapping material 24 can be pre-scored prior to being wrapped around the tow 12 to enable the portion of the acquisition/distribution tube 38 that is scored to be opened by body motion which in use or manually by the wearer prior to use. The wrapping material 24 may be pre-scored prior to being placed on supply roll 25. Alternatively, the feed compression rollers 95 may be equipped with cutting means to produce or cut a series of generally parallel and substantially equal length score lines at proper intervals in the wrapping material 24. This enables an acquisition/distribution tube 38 to be formed having a plurality of generally parallel score lines extending around at least a portion of its periphery, the score lines being located over the window 64 of the absorbent core member 44. Preferably, the score lines generally have the same length which is substantially equal to the length of the window 64.

The wrapping material 24 may also be comprised of a low or no wet strength material which will rupture upon exposure to moisture or humidity and expose the fibers contained in the acquisition/distribution tube 38. Preferably the wrapping material has a wet tensile strength equal to or less than 10 grams per linear inch in the cross machine direction as measured by Tappi Method T 456 om-87.

Additionally or alternatively, the adhesive of the applicator 26 used in the tube forming machine 16 to form and maintain the wrapped cylinder 34 can also be a water-soluble adhesive that when put in a high humidity atmosphere or contacted with body exudate will not maintain its bond, causing the acquisition/distribution tube 38 to open along the overlap of the two longitudinal edges of the wrapping material 24 and release the fibers contained therein. A particularly useful water-soluble adhesive is manufactured by Findley Adhesive, Inc. of Milwaukee, Wis. having product designation 9087-05.

If the water-soluble adhesive application is the sole method of predisposing the wrapping material 24 to open, it is preferred that the overlapped edges of the wrapping material 24 of the acquisition/distribution tube 38 face the window 64 when the acquisition/distribution tube 38 is deposited onto the surface of the absorbent core member 44. This will ensure that the fibers in the acquisition/distribution tube 38 will be released into the window 64, rather than released away from the window 64 when the acquisition/distribution tube opens along the overlapped edges. The overlapped edges are properly positioned, for instance, by first forming and placing the acquisition/distribution tube 38 with its overlapped edge facing away from belt 40 and using the vacuum forces of belt 40 and connection 41 to maintain the proper positioning until the acquisition/distribution tube 38 is picked up from the respective pick-up and lay-down drum 42 or 42' being utilized.

Figure 4:
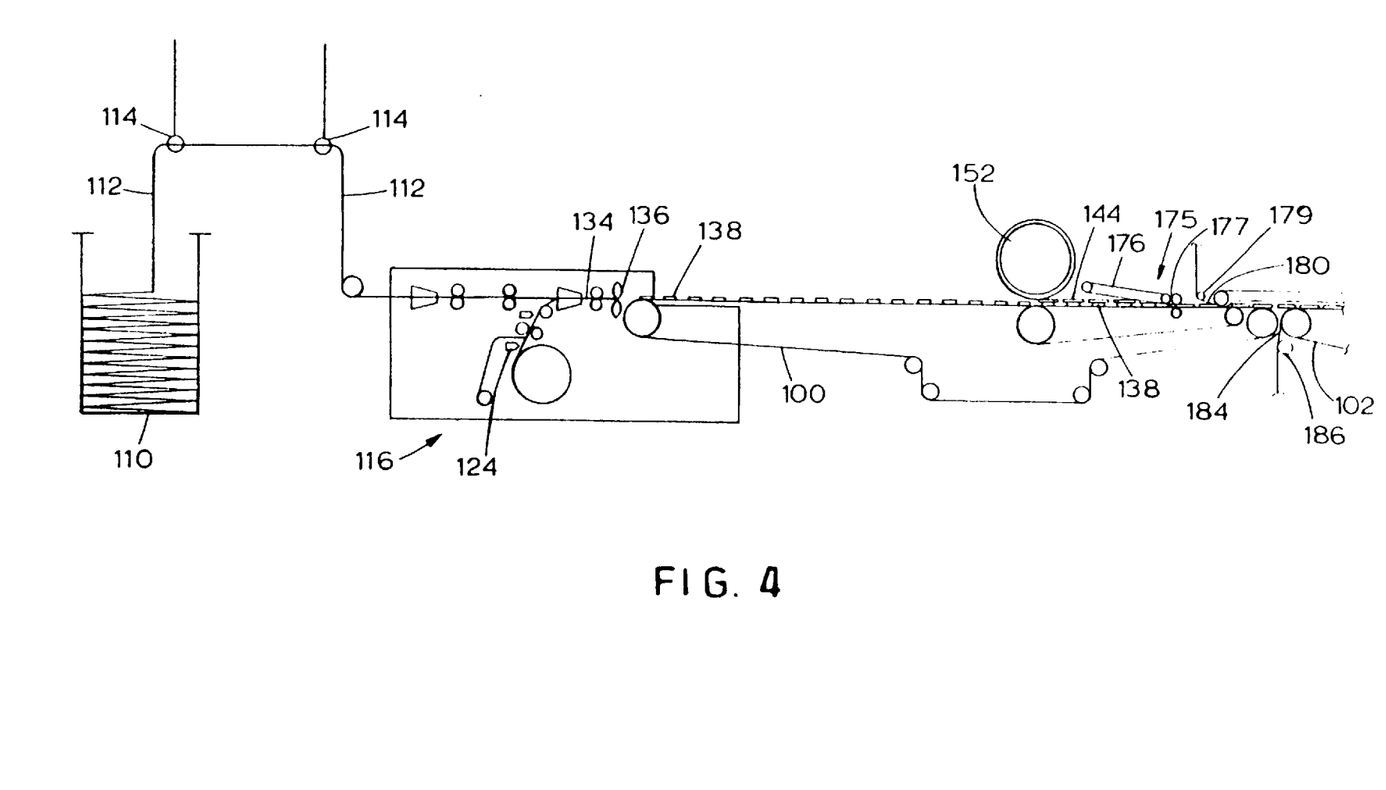
FIG. 4 is a schematic illustration of an apparatus in accordance with a third embodiment of the present invention.

In addition to forming the absorbent product in an acquisition side down manner wherein the acquisition/distribution tube 38 is placed on the absorbent core member 44, an alternative embodiment of the present apparatus is shown in FIG. 4, where the absorbent product is made with the acquisition side up and wherein the core member is laid on top of the tube. Like the apparatus in FIG. 1, a tow 112 of fibers is drawn from a container 110 through a set of guide eyelets 114 and into a tube forming machine 116, similar to the machine 16, where it is wrapped with a wrapping material 124 to form a wrapped cylinder 134 and cut by a cutting element 136 into individual acquisition/distribution tubes 138 as described in connection with the apparatus and process of FIG. 1.

The acquisition/distribution tubes 138 are deposited in spaced relation onto a vacuum conveyer belt 100 which transports the acquisition/distribution tubes 138 to the deposition drum 152 of the absorbent core member former, similar to the machine 46 shown in FIG. 5. The drum 152 may be identical to the drum 52 and has a plurality of equi-spaced deposition cavities about its periphery. The drum 152 deposits an absorbent core member 144 with a window from a cavity onto each acquisition/distribution tube 138, rather than the acquisition/distribution tube being deposited on the absorbent core member as in the embodiment of FIG. 1. Like the embodiment shown in FIG. 1 utilizing the vacuum pick-up and lay-down drum 42, the vacuum belt 100 is moved at a speed greater than that of the wrapped cylinder 134 which is fed to the cutting element 136, to space the acquisition/distribution tubes 138 apart from one another. Preferably, the speed of the belt 100 is set to space the tubes 138 at a distance substantially equal to the distance between the cavities in the drum 152 plus the difference between the length of the acquisition/distribution tubes 138 and these cavities. This enables the belt 100 and the drum 152 to run at the same linear speed so that the drum 152 can properly place the window of absorbent core member 144 onto the acquisition/distribution tube 138. Preferably, a single drive mechanism controls the speed of the belt 100 and the drum 158.

After the absorbent core member 144 has been deposited on the acquisition/distribution tube 138, the two members are transported on conveyer belt 100 to a calendering mechanism 175, similar to mechanism 75, which includes a feed alignment belt 176 and a pair of compression rolls 177 which compress the two members together and press a portion of the acquisition/distribution tube 138 into the window of the absorbent core member 144. After the acquisition/distribution tube 138 and absorbent core member 144 have been compressed, a sheet 180 of topsheet material is fed from a supply roll, around an idler roll 179 onto the top of absorbent core member 144 and the acquisition/distribution tube 138. Downstream of idler roll 179, a sheet 184 of backsheet material is fed from a supply roll around another idler roll 186 under the composite consisting of the sheet 180 of topsheet material, the absorbent core member 144 and the acquisition/distribution tube 138. The composite acquisition/distribution tube 138 and absorbent core member 144 sandwiched between the sheets 180, 184 of topsheet and backsheet materials travel together on conveyer belt 102 to conventional combining and cutting devices to combine and cut the composite into individual absorbent products like those seen in FIGS. 8 and 9. The wrapping material 124 can be predisposed to open by the apparatus and methods discussed above.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. The details of the structure may be varied substantially without departing from the spirit of the invention, and the exclusive use of all modifications which come within the scope of the appended claims is reserved.

What is claimed is:

1. A process of assembling an absorbent article formed of an absorbent core member and a distribution member, the core member having a window opening therein, comprising the steps of:
    a) placing a series of one of said members on a moveable conveyer in spaced relation;
    b) rotating a drum in timed relation with movement of said members on said conveyer, said drum being located above said conveyer and a series of the other of said members being located on a periphery of said drum, said timed relation being such that said other of said members are deposited onto said members while said members are on said conveyer with at least a portion of said distribution member adjacent said window;
    c) depositing said other of the members from said drum onto said members such that at least a portion of said distribution member is adjacent said window;
    d) compressing a portion of said distribution member into said window to combine said members; and
    e) disposing said combined members between a liquid pervious topsheet and a liquid impervious backsheet.

2. The process of claim 1, further including injecting fibers into a deposition cavity of said drum to form said absorbent core member.

3. The process of claim 1, further including cutting a wrapped cylinder to form said distribution member and placing said distribution member on said drum.

* * * * *